United States Patent [19]

Jung et al.

[11] 4,311,851
[45] Jan. 19, 1982

[54] PREPARATION OF CARBOXYLIC ACID ESTERS WITH BF$_3$-ALCOHOL COMPLEX CATALYST

[75] Inventors: John A. Jung, East Hanover, N.J.; Jimmy Peress, West Haven, Conn.

[73] Assignee: Chem Systems Inc., New York, N.Y.

[21] Appl. No.: 105,426

[22] Filed: Dec. 19, 1979

[51] Int. Cl.$^3$ ............................................. C07C 67/38
[52] U.S. Cl. ..................................... 560/233; 203/63; 203/66; 260/410.9 R; 423/206 R; 423/293; 560/214; 560/248; 562/521; 568/6
[58] Field of Search .................... 560/233, 248; 568/6; 203/63, 66; 260/410.9 R

[56] References Cited

U.S. PATENT DOCUMENTS

| | | | |
|---|---|---|---|
| 2,378,009 | 6/1945 | Hanford et al. | 560/233 |
| 2,967,873 | 1/1961 | Koch et al. | 560/233 |
| 3,349,107 | 10/1967 | Pawlenko | 560/233 |

OTHER PUBLICATIONS

Pawlenko, Chemie Ing. Techn., 40,52 (1968).
Moller, Bernstoff-Chemie, 45,129 (1964).

*Primary Examiner*—Vivian Garner
*Attorney, Agent, or Firm*—Bert J. Lewen

[57] ABSTRACT

The invention includes a process wherein an olefin is carbonylated with carbon monoxide to form carboxylic acid esters in the presence of a catalyst complex of one mole of BF$_3$ and one mole of alcohol, and the catalyst is recovered from the desired reaction product and the reaction by-products and is recycled. The carbonylation is carried out until approximately one-half of the alcohol is consumed to form a reaction mass containing the BF$_3$, the alcohol, and carboxylic acid esters in a 2:1:1 molar ratio. In the first step, the one mole of free BF$_3$ is vaporized from the reaction mass. The remaining admixture is a 1:1:1 mixture of the aforesaid compounds. To this mixture additional alcohol is added and the mixture is subjected to distillation. An azeotrope of the product carboxylic acid ester and the alcohol and residual alcohol are removed by the distillation, leaving a residue containing a 1:2 BF$_3$/ alcohol complex and the by-product carboxylic acid esters, which are heavier than the product carboxylic acid ester. The by-products are removed from the residue via solvent extraction and the remaining complex may be combined with an additional mole of BF$_3$ to form the 1:1:1 catalyst complex used in the carbonylation. The additional mole of BF$_3$ is preferably that initially separated from the reaction mass; however, it may be obtained from an external source. The reconstituted catalyst is then preferably recycled to the carbonylation reaction. The carboxylic acid ester/alcohol mixture may be separated by azeotropic distillation using an azeotroping agent, such as octane, to recover the alcohol-octane as overhead product and the carboxylic acid ester as bottoms product.

6 Claims, No Drawings

PREPARATION OF CARBOXYLIC ACID ESTERS WITH BF₃-ALCOHOL COMPLEX CATALYST

This invention relates to the recovery and recycle of a $BF_3$.alcohol catalytic complex used in the carbonylation of olefins to form carboxylic acid esters.

It has long been desired to find an inexpensive means of making alkyl methacrylates and alkyl acrylates, basic monomers for the formation of acrylic resins, as well as acrylic and methacrylic acids. Conventionally, methyl methacrylate is prepared by reacting acetone and hydrogen cyanide to form cyanohydrin; dehydrating the cyanohydrin in the presence of sulfuric acid to form methacrylamide sulfate; and finally reacting the sulfate with methanol and sulfuric acid to form the desired methyl methacrylate. Because of the high cost of the raw materials and the need to dispose of the by-product ammonium sulfate, this process is deficient.

Other proposed processes for making methyl methacrylate and methacrylic acid involve isobutylene oxidation, ammoxidation, epoxide formation and t-butanol oxidation. These processes also suffer from high capital costs and, in some cases, high raw material costs.

In our U.S. Pat. application Ser. No. 28,460, filed Apr. 9, 1979, now U.S. Pat. No. 4,256,913, which is hereby incorporated by reference herein, it is proposed to prepare acrylic acid, methacrylic acid and corresponding esters from olefins and carbon monoxide in the presence of a catalytic complex composed of one mole of $BF_3$ and one mole of either water or an alcohol, as the case may be. Where the olefin is propylene, for example, the product is methyl isobutyrate if methanol is used and methacrylic acid if water is used. The methyl isobutyrate may be dehydrogenated to prepare the methyl methacrylate. In this process the end products are formed from readily available raw materials, no by-products are formed, and the capital costs are economically attractive. The process described in the aforesaid application while extremely attractive for the foregoing reasons was seen to originally suffer from the drawback that the catalyst could not be easily recovered for reuse. As a matter of fact, in discussing this type of catalyst for use with cyclic olefins, for example, Moller, in Brennstoff-Chemie 45, 129 (1964), said that the catalyst $BF_3$—$CH_3OH$ would be of little interest because it could not be recovered in usable form. This is because there was no known way to separate the ester product from the catalytic complex without destroying the $BF_3$, e.g., by hydrolyzing it with water to form fluoboric acids.

Similarly, in U.S. Pat. No. 2,967,873 to Koch et al., issued Jan. 10, 1961, the difficulties inherent in recovering catalysts of the sort noted above are discussed. Although Koch et al. disclose a way of recovering such catalysts, the process of the U.S. Pat. No. 2,967,873 patent requires (a) that *both* water and alcohol be employed in the catalyst and (b) that the olefin starting material contain no fewer than six carbon atoms. Otherwise, it is said, the catalyst cannot be separated out cleanly.

U.S. Pat. No. 3,349,107 to Pawlenko, issued Oct. 24, 1967, discloses use of a two-phase liquid system in a pressure reactor in the synthesis of carboxylic acids and their methylesters from starting materials including olefins having at least four carbon atoms, CO and ROH, where R is hydrogen or $CH_3$. One of the liquid phases comprises olefin, solvent and product and the other includes a catalyst and the ROH. A suggested catalyst is the complex $[ROH_2][BF_4]$ and the solvent used is heptane.

U.S. Pat. application Ser. No. 28,458, filed Apr. 9, 1979, now U.S. Pat. No. 4,262,138, which is hereby incorporated by reference herein, discloses a process for preparing low molecular weight saturated carboxylic acid esters from ethylene and propylene by carbonylation with carbon monoxide and a catalytic complex composed of one mole of $BF_3$ and one mole of an alcohol. More specifically, the invention of the Ser. No. 28,459 application relates to the recovery and recycle of the catalyst in a convenient and economical manner. In the process of that invention, the olefin is carbonylated with carbon monoxide in the liquid catalyst complex until substantially one-half of the alcohol is consumed. This results in the formation of a reaction mass consisting of the carboxylic acid ester, the alcohol, and the $BF_3$ in a molar ratio of 1:1:2 which is then subjected to a distillation step wherein one-half of the $BF_3$ is removed as a distillate fraction. The bottoms product from this step is said to consist of the same components in a molar ratio of 1:1:1. This mixture is then recommended to be further distilled after sufficient additional alcohol is added to form a low boiling azeotrope with all of the carboxylic acid ester, with recovery of the azeotrope as an overhead product. The residue material remaining is described as a $BF_3$/alcohol 1:2 complex which may be easily reconstituted to form the 1:1 catalytic complex by the addition of free $BF_3$, which may be that $BF_3$ initially separated from the reaction mass.

Thus the Ser. No 28,459 application can be said to describe a process for the carbonylation of an olefin selected from the group consisting of ethylene and propylene which comprises reacting the olefin with carbon monoxide in the presence of a catalyst complex containing equimolar amounts of $BF_3$ and alcohol, carrying out said reaction until about 50% of the alcohol in said catalyst is consumed, thereby forming a carboxylic acid ester and liberating free $BF_3$; separating sufficient $BF_3$ from the reaction mass to leave a first residue containing equimolar amounts of the $BF_3$, the alcohol and the carboxylic acid ester; admixing the first residue with additional alcohol; thereafter distilling said admixture to separate overhead an azeotrope of said alcohol and said carboxylic acid ester and additional uncomplexed alcohol until a second residue containing $BF_3$ to alcohol in a molar ratio of 1:2 remains; and thereafter combining said second residue with additional $BF_3$ to form the catalyst complex.

It has now been found that in addition to the $BF_3$:alcohol complex in a 1:2 molar ratio, the above-mentioned second residue also contains "heavy ends" products of the carbonylation reaction. These by-products are primarily esters of branched acids and where, for example, the olefin feed is propylene and the catalytic complex employed is $BF_3.CH_3OH$, the by-products are primarily esters of branched acids having carbon numbers of $C_{4+3n}$ where $n=1$, 2, 3, and so forth, with the major components being α, α-dimethyl methyl valerate (DMMV) and methyl neodecanoate (MND). In a continuous process operation, such by-products must be purged from the system to prevent their build-up in the process streams.

Atmospheric distillation to effect separation and removal of ester by-products of the sort noted above would lead to decomposition of the catalytic complex. In the example of the preceding paragraph, for example, a dimethyl ether complex and BF$_3$.2H$_2$O would be formed. Distillation at reduced pressure and lower temperature would effect some but not total separation of by-product and catalyst, since the boiling point of some by-product and the catalytic complex would be the same, but the cost of maintaining the requisite low pressure would render such a process economically uncompetitive. The by-products could be separated via a water quench, but this too would decompose the catalyst and recovery of BF$_3$ from excess water would be very expensive.

Contrary to the expectation one would have from the prior art, the catalyst herein can be recovered even though no water is present and propylene is used as feed olefin. The process of this invention permits the recovery of the catalyst from the second residue in the form in which it is there found, the reconstitution of such catalyst to the desired catalytic complex, and the recycle of the catalytic complex to the reactor while, at the same time, effecting removal of the undesired by-products, i.e., the previously mentioned branched acid esters in the context of the above example.

We have found favorable partition coefficients to exist vis-a-vis the by-products to be separated from the catalyst and certain solvents for such by-products which have negligible mutual solubility with the catalyst. A difference in boiling point between the extraction solvent and the by-product(s) is desired so that the two may be readily separated. Furthermore, it is preferred that the solvents be in liquid form at room temperature to facilitate handling. in addition, it is preferred that the solvents have a normal boiling point above about 60° C. to enable condensation with cooling water. Suitable solvents include paraffins, both straight chain and branched, having from 6 to about 20 carbon atoms or 6–14 carbon atoms. Preferred solvents include heptanes and octanes. The most highly preferred embodiment utilizes n-octane.

The manner in which the extraction solvent is employed to free the catalyst/alcohol complex of by-products and the specific solvent used will vary with the particular process equipment, conditions and reactants selected. We prefer a continuous rather than, for example, batch process for the carbonylation reaction and therefore prefer to conduct the stripping of by-products from the catalyst/alcohol complex of the second residue via continuous countercurrent liquid-liquid exchange, and, in the production of methyl isobutyrate from propylene, n-octane is the preferred solvent because its boiling point matches well with the rest of the process.

In a preferred embodiment of the present invention, gaseous feedstocks consisting of either propylene or ethylene and carbon monoxide are used. The olefins may be obtained from any source, most generally from steam cracking of hydrocarbons. The carbon monoxide employed should have a purity of at least 99%, though mixtures of carbon monoxide and other inert gases, such as carbon dioxide, may be used. It is preferred that the olefin and carbon monoxide be of high purity since this will simplify product recovery and minimize losses in purge streams required to remove inerts from the reaction system.

The reaction may be carried out at temperatures of from 0° C. to 100° C., preferably from 20° C. to 60° C. The temperatures should be kept at moderate levels throughout the process because high temperatures favor the formation of by-products, especially heavier esters.

In the carbonylation reaction of the invention, one mole of carbon monoxide reacts with each mole of olefin. This is known as the external reactant ratio. On the other hand, it is desirable to maintain a large molar excess of carbon monoxide in the vapor phase in order to suppress undesirable side reactions. This ratio (known as the internal carbon monoxide to olefin molar ratio) is controlled by the system pressure, degree of agitation and purge rate and is broadly at least 5:1, preferably at least 8:1. As a practical matter, ratios of not more than 1000:1, preferably not more than 100:1, are used.

In view of the foregoing, it will be understood that in a batchwise process and during the start-up of a continuous process a large molar excess of the carbon monoxide is fed. However, in the continuous process, once steady state conditions are achieved, only about one mole of carbon monoxide is fed to the reactor for each mole of olefin.

The reaction pressure, while not critical, is generally of from 10 to 300 atmospheres, most preferably from 30 to 100. While higher pressures are not detrimental and in some instances actually favor selectivity to the desired products, again practical considerations such as equipment design and safety factors favor the use of the pressure ranges set forth above.

The selection of the appropriate catalyst complex is an essential feature of the invention. As pointed out previously, the catalyst complex used in the instant invention contains equal molar amounts of BF$_3$ and an alcohol. These catalysts are stable complexes having specific physical properties. They exist as liquids at room temperature and therefore can be conveniently used as the reaction solvent.

While it is understood that the 1:1 molar ratio catalyst is the active constituent in the instant invention, the catalyst may be prepared using ratios of from about 0.75 to 10 moles of BF$_3$ for each mole of the alcohol, preferably from 0.75 to 2 moles per mole. It will be understood that, when less than one mole of the BF$_3$ is utilized with, say, methanol, the catalyst is a mixture of BF$_3$.CH$_3$OH and BF$_3$.2CH$_3$OH. This latter compound is also a stable complex; however, in contrast to the 1:1 molar ratio catalyst, it is non-selective to the desired product and of relatively low activity. Accordingly, a substantial amount of such complex is undesirable.

On the other hand, where the molar ratio is in excess of 1:1, the 1:1 catalyst complex (e.g., BF$_3$.CH$_3$OH) is in admixture with uncomplexed BF$_3$. Since excess BF$_3$ is not catalytically active for the desired ester, sizeable excesses are of little advantage.

As noted above, in performing the process of the invention it is advantageous to use the catalyst as the reaction medium. Other organic constituents may be present, so long as they do not interfere with the carbonylation. The reaction period is not critical, but should be selected so as to achieve acceptable conversions without unduly lengthening the process cycle. As a practical matter, the reaction period ranges from about 10 minutes to 3 hours.

Generally, it is preferred to select the alcohol component for the catalyst from the lower alkyl alcohols having from 1 to 4 carbon atoms. These include methanol, ethanol, propanol, isopropanol, and n-butanol and its isomers. Additionally, other alcohols can be used. These include alkyl alcohols having from 5 to 12 carbon atoms and aralkyl alcohols such as benzyl alcohol, alpha-phenethyl alcohol and beta-phenethyl alcohol.

In addition, it has been found that other catalyst additives, such as hydrogen fluoride, sulphuric acid and phosphoric acid, are not necessary for the synthesis of the desired products.

The products of the carbonylation may be dehydrogenated by several known procedures such as described in Japan Kokai No. 78 82,720 or Japan No. 73 19,614 where carbonylation products such as, for example, methyl isobutyrate, are oxidatively dehydrogenated at 300° C. and 1 atm. pressure with oxygen-containing gases over catalysts composed of mixed metal oxides, the major component being molybdenum oxide. In U.S. Pat. No. 3,721,705, methyl isobutyrate is oxidatively dehydrogenated at 500° C. in the presence of sulfur. In British Pat. No. 1,141,625, a dehydrogenation is carried out without added oxidizing agents over alumina catalysts at 600° C. and reduced pressure.

In the production of methyl isobutyrate, a most preferred use for the process of the invention, the olefin used is propylene and the catalyst complex used contains equal molar amounts of boron trifluoride and methanol. This catalyst is a stable complex having specific physical properties. It exists as a liquid at room temperature and therefore can be conveniently used as the reaction solvent.

To produce methyl isobutyrate, the carbonylation is continued until one-half of the methanol is consumed in the formation of the methyl isobutyrate product. The resulting product mixture has a composition consisting of methyl isobutyrate, methanol and $BF_3$ in a molar ratio of about 1:1:2, along with some by-products as previously described.

This reaction mass is stripped in a countercurrent contacting tower to separate half the $BF_3$ contained therein as a vapor overhead product and to produce a residue product containing approximately equimolar amounts of methyl isobutyrate, methanol and $BF_3$ (hereinafter the "1:1:1 complex") plus the by-products. Operating conditions for this step depend on the vapor-liquid equilibria for the system and can be varied over a wide range of temperatures and pressures. The separation is conveniently done at ambient pressure and at approximately 85° C., the boiling point of the 1:1:1 complex. Under these conditions, the stripping action is provided by the boiling 1:1:1 complex vapors which are generated in the bottom of the stripping column. These vapors flow countercurrently to the reaction mixture feed which is fed at the top of the column. Alternatively, the column can be operated at a temperature and pressure wherein the 1:1:1 complex does not boil by using an inert stripping gas, e.g., nitrogen, introduced at the bottom of the column. Generally, it is preferred to maintain the column temperature below 100° C. to minimize by-product formation.

After the separation of the $BF_3$, the residue contains approximately equimolar quantities of $BF_3$, methanol and methyl isobutyrate along with by-products. The methyl isobutyrate and the $BF_3$ contained in this residue from the stripping step cannot readily be recovered by means known to the art without destroying the catalyst complex. For example, $BF_3$ or the organic components cannot be preferentially stripped from this complex, nor are there any known extraction techniques which will preferentially extract the $BF_3$ or the organic components. Methods known to the art for making the separation involve reaction of the $BF_3$ with another component, e.g., water or sodium chloride. In the first case hydrolysis of the $BF_3$ occurs with release of the organic components. In the second case a $BF_3$/sodium chloride compound is formed with release of the organic components. However, there is no known practical method for recovering the $BF_3$ from the $BF_3$ hydrolysis compounds or the $BF_3$/sodium chloride compound.

To separate the desired components, methanol is added to the 1:1:1 complex, preferably in a distillation zone. The amount of methanol added corresponds to at least that required to produce a methyl isobutyrate/methanol azeotrope as an overhead product and a bottoms product comprising a complex of $BF_3/CH_3OH$ in 1:2 molar ratio. The composition of this azeotrope, an atmospheric pressure, is 75 weight percent methanol, 25 weight percent methyl isobutyrate. This is equivalent to a methanol/methyl isobutyrate molar ratio of 9.56. Thus, if the distillation is conducted at ambient pressure, at least 10.56 additional moles of methanol must be added to the distillation zone. Technically there is no upper limit to the amount of methanol that can be added. The amount that is added is dictated by the design of the distillation equipment wherein energy requirements are balanced against equipment costs.

The separation is conveniently carried out in a conventional continuous distillation column containing trays or packing. The 1:1:1 complex is generally fed near the middle of the column with the methanol added above this feed point. The distillate fraction from this column is a low boiling methanol/methyl isobutyrate azeotrope and any additional uncomplexed methanol. The bottoms product is a $BF_3$/methanol complex in 1:2 molar ratio. Operating temperatures and pressures for the column are a function of the vapor pressure-temperature curve for the complex since this is the material boiling in the reboiler. Typical pressure-temperature data is given below:

| Temperature, °C. | Vapor Pressure, mm Hg |
|---|---|
| 57 | 4 |
| 130 | 100 |
| 200 | 760 |

Preferrred operating temperatures are from 50° to 200° C. These temperatures minimize side reactions which can lead to yield losses and complicate subsequent purification steps.

The bottoms stream from the column comprises $BF_3$ and methanol in 1:2 complex form and contains "heavy ends" products of the carbonylation reaction of the sort previously described. Removal of the by-products from the $BF_3$/methanol complex is carried out by continuous countercurrent liquid-liquid extraction, preferably using n-octane as the extracting solvent. The $BF_3$/methanol 1:2 complex is then reconstituted to the 1:1 complex, preferably via recombination with the $BF_3$ originally separated from the reaction mass. The 1:1 complex is the active catalyst and it is recycled to the carbonylation reactor.

The methyl isobutyrate and methanol distillate from the column may be separated by any conventional means. In one particular technique, azeotropic distillation is used wherein a liquid paraffin, preferably having a boiling point of 30° C. to 150° C., is added to form a low boiling azeotrope with the methanol, with n-octane being a preferred paraffin. The ambient pressure boiling point of the octane/methanol azeotrope is approximately 65° C., while the methyl isobutyrate has an ambient pressure boiling point of approximately 90° C. The methyl isobutyrate remains behind as a residue and the azeotrope is removed overhead and condensed. This condensate is then mixed with water in a separate vessel wherein an aqueous methanol phase and a paraffin phase, essentially free of methanol, are formed. The organic phase is recycled to the azeotropic distillation column. The aqueous methanol phase is then further distilled to recover methanol as an overhead product for recycle to the aforementioned $CH_3OH$/methyl isobutyrate column.

The methyl isobutyrate product of the carbonylation may be dehydrogenated by several known procedures such as described in U.S. Pat. No. 3,721,705 and British Pat. No. 1,141,625 using conventional dehydrogenation catalysts.

To illustrate even more fully the instant invention, attention is directed toward the following example:

EXAMPLE I

To a 600 ml. stirred autoclave at 20° C. is added 100 g. of a $BF_3 \cdot CH_3OH$ catalyst. A 9:1 carbon monoxide/propylene mixture is added to the autoclave at 60 atm. The mixture is heated to 50° C. and held at this temperature for one hour. A sample taken from the autoclave is analyzed by a gas-liquid chromatography. All of the propylene is converted and the selectivity to methyl isobutyrate is 94%. The atoclave is cooled, depressurized, and then repressurized again to 60 atm. with the 9:1 gas mixture. This procedure is repeated several times until about 50% of the methanol in the catalyst reacts. The mixture remaining in the autoclave is again analyzed and found to be approximately a 2:1:1 mixture of boron trifluoride/methanol/methyl isobutyrate (about 34 wt. % isobutyrate). Analysis indicates the overall selectivity of the reaction to be about 88.8 percent methyl isobutyrate, about 7.4 percent $C_7$ acid esters and about 3.8 percent $C_{10}$ acid esters, with the latter two being principally α, α-dimethyl methyl valerate (DMMV) and methyl neodecanoate (MND) respectively.

The reaction mass is then treated in accordance with the following sequence: The reaction mixture is introduced into a distillation flask wherein the liberated $BF_3$ is removed overhead at a temperature of 60° C. and a pressure of 100 mm Hg. This $BF_3$ is recycled for recombination with the $BF_3$ left behind and eventual reuse in the autoclave as hereinafter described.

This leaves in the distillation flask a solution containing approximately a 1:1:1 ratio $BF_3$/methanol/methyl isobutyrate complex plus by-products. To this, sufficient methanol is added to convert the solution to a 1:10:1 molar ratio. The resulting solution is distilled at a pressure of 10 mm Hg until the overhead temperature reaches 80° C. to separate a methyl isobutyrate/methanol azeotrope which is collected as a solution. Continued distillation at 80° C. removes additional methanol.

The residue of the distillation weighs 69.2 grams. It consists of a $BF_3$/methanol complex in a molar ratio of 1:2 and contains 3.8% DMMV and 1.6% MND. To this mixture is added an equivalent volume of n-octane and the mixture is stirred for 20 min. to ensure intimate mixing of the two layers. The mixture is allowed to stand and separate and the octane layer separated. This procedure is repeated twice, each time using an equivalent volume of n-octane for extraction. Analysis of the catalyst phase reveals that about 75% of the DMMV and 85% of the MND are removed.

To the catalyst phase is added 33.9 grams of $BF_3$ to obtain the 1:1 complex, which is used for carbonylating propylene under the aforementioned conditions. The mixture recovered from the autoclave contains about 33 wt. % of methyl isobutyrate. Analysis of the product indicates the selectivity of the reaction to be about 85% methyl isobutyrate.

N-octane is added to the methyl isobutyrate/methanol solution and a low boiling azeotrope of methanol and octane is distilled overhead. The residue is methyl isobutyrate, which may be dehydrogenated to form methyl methacrylate.

EXAMPLE II

To $BF_3 \cdot 2CH_3OH$ was added enough α,α-dimethyl methyl valerate (DMMV) to form a solution containing 13.2% DMMV in $BF_3 \cdot 2CH_3OH$. To this solution was added one-half its volume of n-octane and the mixture was stirred 20 min. to ensure intimate mixing of the two layers. The mixture was allowed to stand and separate and the octane layer was removed and analyzed. This procedure was twice repeated, each time using one-half volume of n-octane for extraction. Analysis revealed favorable partition coefficients (K) as illustrated below:

| Extraction No. | Wt. % DMMV in Solvent | K* |
|---|---|---|
| 1 | 9.89 | 1.00 |
| 2 | 7.88 | 1.09 |
| 3 | 6.07 | 1.34 |

$$*K = \frac{\text{Wt. \% Ester in Extraction Solvent}}{\text{Wt. \% Ester Remaining in Catalyst}}$$

EXAMPLE III

To $BF_3 \cdot 2CH_3OH$ was added enough α, α-dimethyl methyl valerate (DMMV) to form a solution containing 13.9 wt. % DMMV in $BF_3 \cdot 2CH_3OH$. To this solution was added one-half its volume of n-heptane and the mixture was stirred for 20 minutes to ensure intimate mixing of the two layers. The mixture was allowed to stand and separate and the heptane layer was separated and analyzed. This procedure was twice repeated, each time using one-half volume of n-heptane for extraction. Analysis revealed favorable partition coefficients as illustrated below:

| Extraction No. | Wt. % DMMV in Solvent | K |
|---|---|---|
| 1 | 12.2 | 1.22 |
| 2 | 8.2 | 1.13 |
| 3 | 5.5 | 0.96 |

EXAMPLE IV

To $BF_3 \cdot 2CH_3OH$ was added enough methyl neodecanoate (MND) to form a solution containing 9.2 wt. % MND in $BF_3 \cdot 2CH_3OH$. A single extraction with n-octane resulted in partition coefficient of 4.14.

EXAMPLE V

To BF$_3$.2CH$_3$OH was added enough methyl neodecanoate (MND) to form a solution containing 8.5 wt. % MND in BF$_3$.2CH$_3$OH. A single extraction with n-heptane performed as in Example III resulted in a partition coefficient of 1.4.

A direct method of recovering the catalyst components has been attempted but was not found successful. For example, a molar excess of sodium chloride was added to the admixture of BF$_3$/methanol/methyl isobutyrate 1:1:1 complex in an attempt to form a complex of the BF$_3$ with the sodium chloride and separate the complex. In this procedure, the methyl isobutyrate and methanol were easily separated by distillation from the mixture thus formed. However, the BF$_3$/sodium chloride complx salt, even after heating to 400° C., did not completely break down into its component salts. Analysis of the BF$_3$ thus recovered indicates that only 50% of the initital F$_3$ present was recovered.

Still aother approach to separating the 1:1:1 complex was to use n-heptane to selectively extract the methyl isobutyrate. Only about 10% of the methyl isobutyrate was extracted into the heptane after extraction with one volume of the heptane for two volumes of the complex.

In still another approach, an admixture of BF$_3$/methanol/methyl isobutyrate in a molar ratio of 1:1:0.5 was introduced to the top of a countercurrent stripping column while nitrogen was passed through the bottom of the column under atmospheric pressure at a temperature of 80° C. The effort to preferentially strip the BF$_3$ was unsuccessful. Analysis showed that no BF$_3$ was removed by this technique.

We claim:

1. In a process for preparing a carboxyalic acid ester wherein an olefin selected from the group consisting of ethylene and propylene is reacted with carbon monoxide in the presence of a catalyst complex containing an equimolar amount of BF$_3$ and alcohol, with substantially no water, at a temperature of from 0° to 100° C. and at an internal carbon monoxide-to-olefin molar ratio of from 5:1 to 1000:1 to form a product carboxylic acid ester, by-product carboxylic acid esters and BF$_3$, wheren sufficient BF$_3$ is stripped from the reaction mass to form a first residue containing substantially equimolar amounts of BF$_3$, the alcohol, and the product carboxylic acid ester plus by-product carboxylic acid ester, and wherein additional alcohol is added to the first residue to form an admixture which is distilled until a second residue containing said by-product carboxylic acid esters and BF$_3$-alcohol complex in a molar ratio of 1:2 remains and thereafter combining said second residue with additional BF$_3$ to form the catalyst complex, the improvement of removing said by-product carboxylic acid esters from said second residue by solvent extraction before adding BF$_3$ to said second residue, said solvent being a paraffin having from 6 to 20 carbon atoms.

2. The process of claim 1 wherein the olefin is propylene, the catalyst is BF$_3$.CH$_3$OH, and the product carboxylic acid ester is methyl isobutyrate.

3. The process of claim 1 or 2 wherein the extraction solvent is n-octane.

4. The process of claim 1 wherein the second residue after solvent extraction is combined with the stripped BF$_3$ to form the catalyst complex.

5. In a process for preparing methyl isobutyrate wherein propylene is reacted with carbon monoxide in the presence of a catalyst complex containing an equimolar amount of BF$_3$ and methanol, with substantially no water, at a temperature of from 20° to 60° C. and at an internal carbon monoxide-to-propylene molar ratio of from 8:1 to 100:1 to form product methyl isobutyrate, by-product carboxylic acid esters and BF$_3$, wherein sufficient BF$_3$ is stripped from the reaction mass to form a first residue containing substantially equimolar amounts of BF$_3$, methanol, and methyl isobutyrate plus by-product carboxylic acid esters, and wherein additional methanol is added to the first residue to form an admixture which is distilled until a second residue containing said by-product carboxylic acid esters and BF$_3$.2CH$_3$OH remains and thereafter combining said second residue with additional BF$_3$ to form the catalyst complex, the improvement of separating said by-product carboxylic acid ester from said BF$_3$.2CH$_3$OH by solvent extraction, said solvent being a paraffin having from 6 to 14 carbon atoms, combining the separated BF$_3$.2CH$_3$OH with the BF$_3$ stripped from the reaction mass to form BF$_3$.CH$_3$OH, and recycling said last-mentioned BF$_3$.CH$_3$OH for use in said carbonylation.

6. The process of claim 5 wherein the extraction solvent is n-octane.

* * * * *